US00PP22433P2

(12) United States Plant Patent
Horvath

(10) Patent No.: US PP22,433 P2
(45) Date of Patent: Jan. 3, 2012

(54) ***GEUM* PLANT NAMED 'MAI TAI'**

(50) Latin Name: ***Geum* hybrid**
Varietal Denomination: Mai Tai

(76) Inventor: Brent Horvath, Fontana, WI (US)

( * ) Notice: Subject to any disclaimer, the term of this patent is extended or adjusted under 35 U.S.C. 154(b) by 0 days.

(21) Appl. No.: 12/924,967

(22) Filed: Oct. 12, 2010

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Annette Para

(57) ABSTRACT

A new, distinct *Geum* plant as shown and described, characterized by single and semi double flowers that open vermilion then fade to peach and then finally fade to pink.

2 Drawing Sheets

Figure 1:
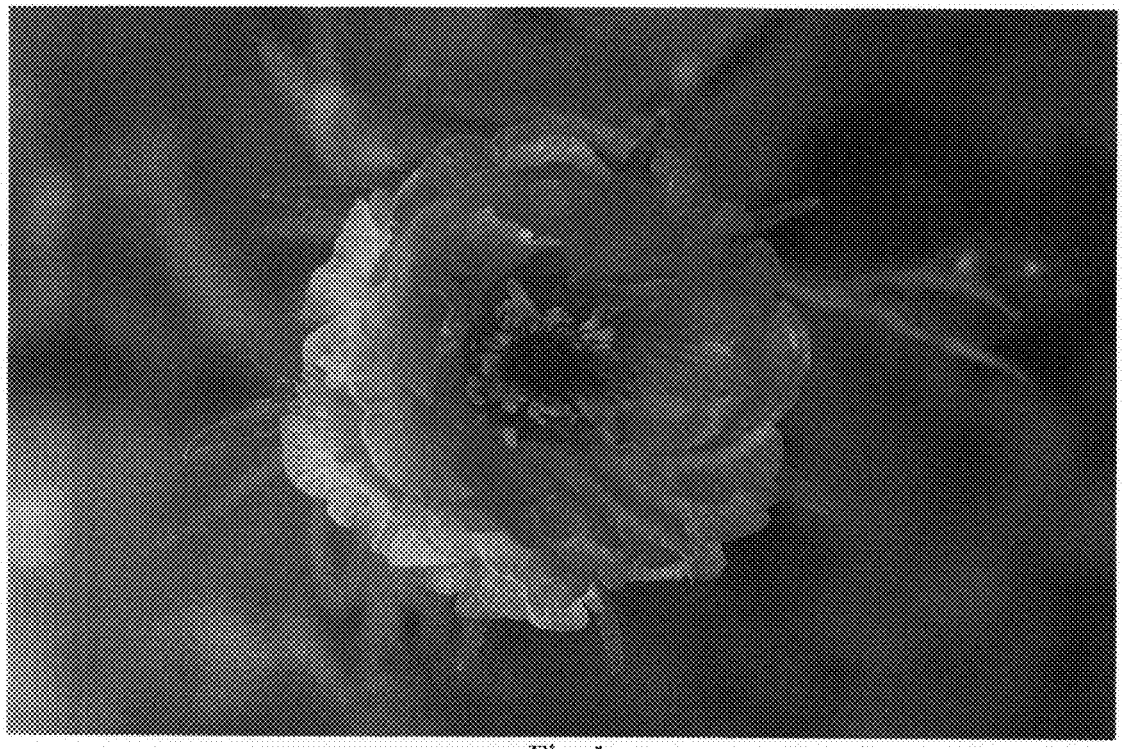

Latin name: *Geum* hybrid.
Cultivar name: 'Mai Tai'.

BACKGROUND OF THE INVENTION

The present invention relates to a new and distinct hybrid of *Geum* plant named 'Mai Tai' characterized by single to semi double flowers that open vermilion then fade to peach and then finally fade to pink. The new *Geum* was raised as a seedling from a controlled cross of *Geum* Mango Lassi, not patented, and *Geum* 'Flames of Passion' U.S. Pat. No. 13,730, patented, in Hebron, Ill. in 2005. The selection of the new plant was due to its' unique and multi colored single and semi double flowers that open vermilion then fade to peach and then finally fade to pink. Asexual division have been the means of reproduction. The intial division propagation has taken place at a nursery Hebron, Ill. since 2006. The new *Geum* has shown to be stable and identical in reproduction to the parent after dividing over 70 two year old plants resulting in over 700 divisions from 2006 to 2009.

SUMMARY OF THE INVENTION

In the following description, color references are made to The Royal Horticultural Society Colour Chart (2001). The new *Geum* plant named 'Mai Tai' characterized by single and semi double flowers of RHS 53B fading to 48C and finally to 36B and 36C compared to the parents have been observed to be unique and stable.

Plants of the new *Geum* can be compared to plants of female or seed parent *Geum* 'Flames of Passion' U.S. Pat. No. 13,730, patented. 1. The new plant flower colors are 53B which fades to 36B and 36C and finally to 48C while *Geum* 'Flames of Passion' has a red flower color 179 A.

Plants of the new *Geum* can also be compared to the female or seed parent plant *Geum* 'Mango Lassi', not patented. 1. The new plant flower colors are 53B which fades to 36B and 36C and finally to 48C while *Geum* 'Mango Lassi' has a golden yellow 14 B and orange red 44 A flower color.

DESCRIPTION OF PHOTOGRAPHS

FIG. 1. Close up of the flower when it opens. RHS 53B

Figure 2:
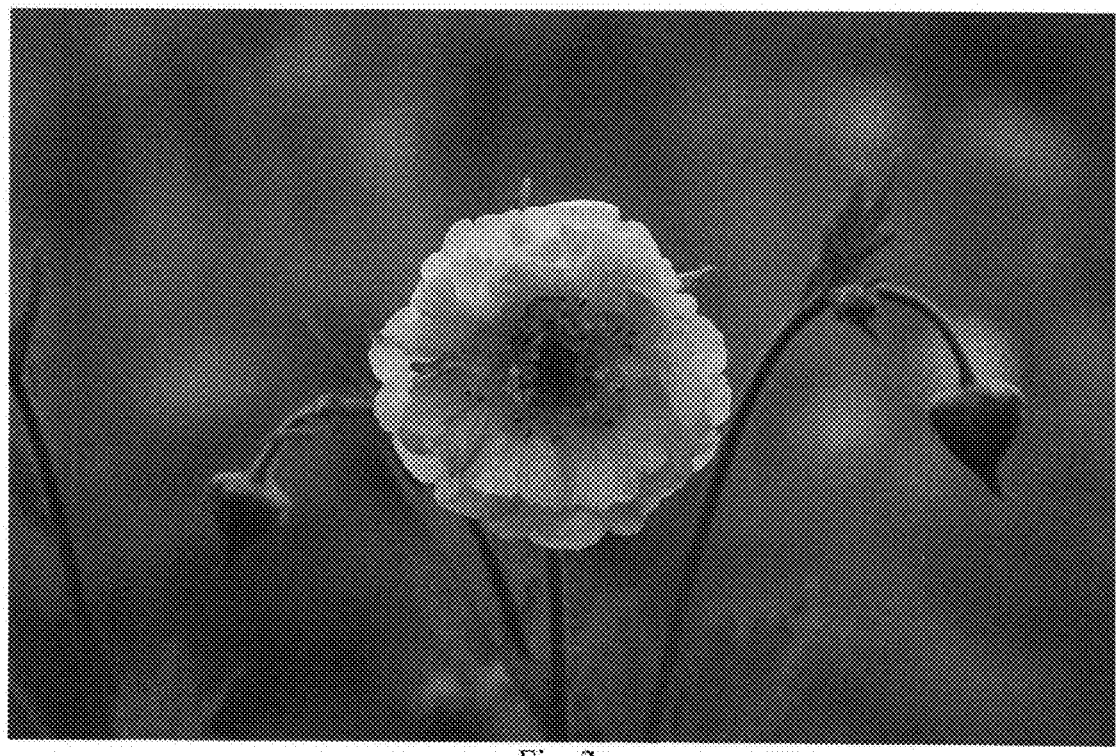
Figure 3:
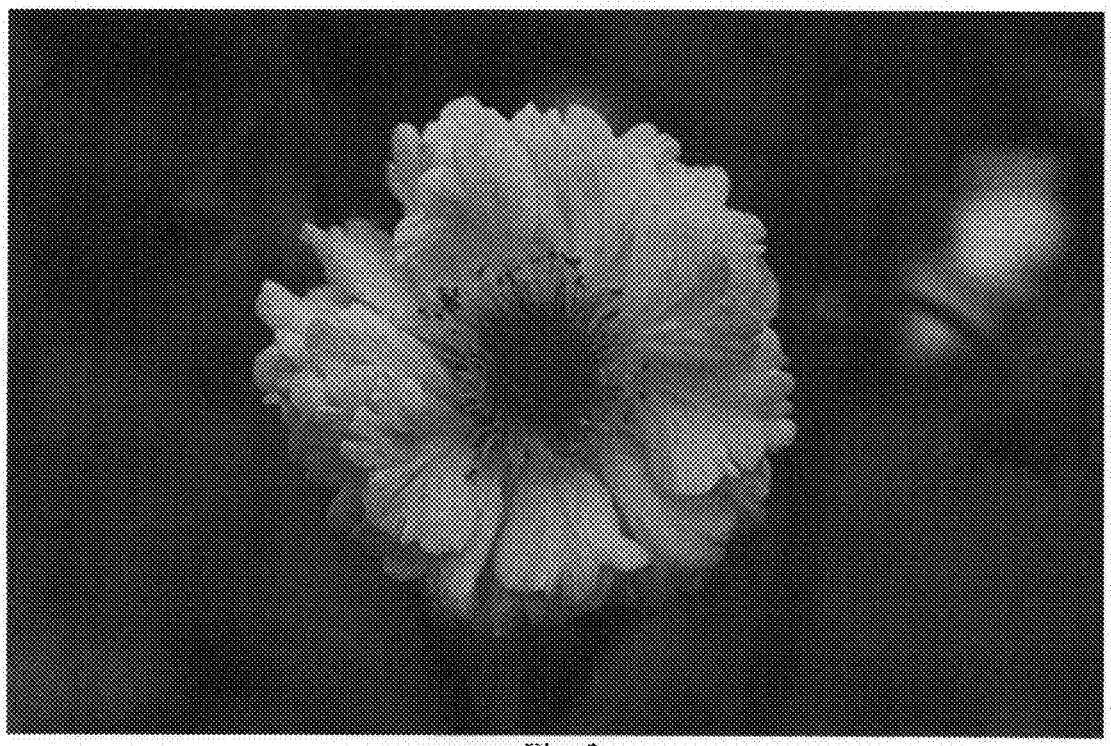
Figure 4:
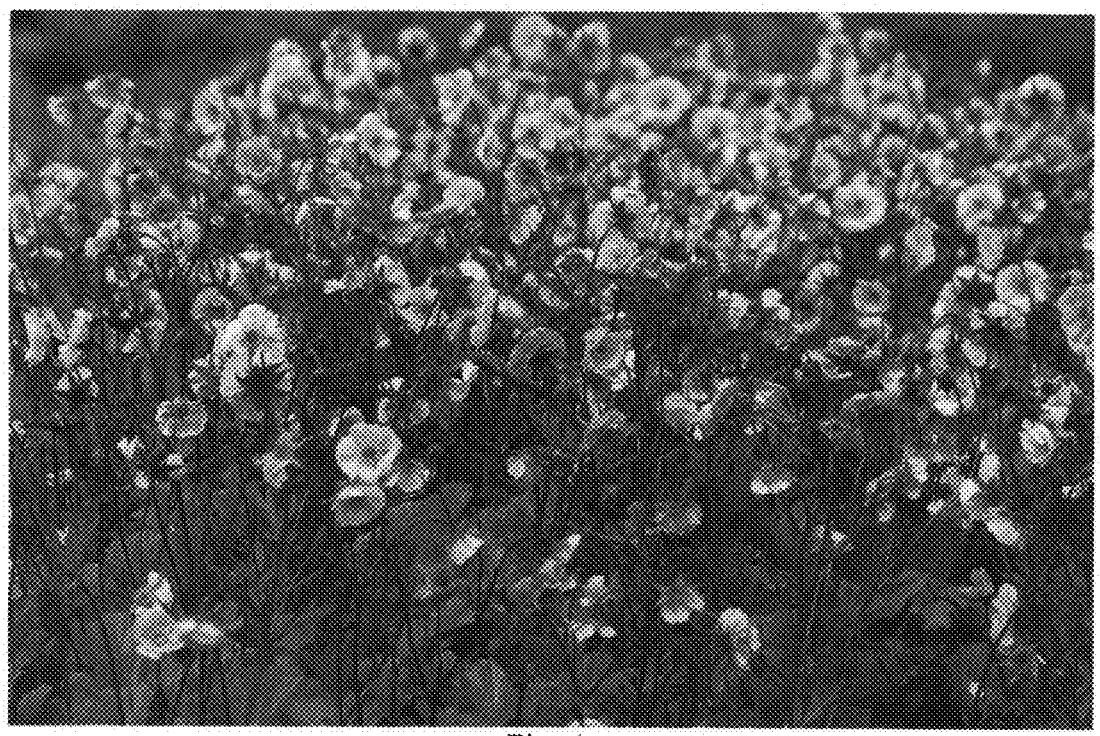

FIG. 2. Close up of the flower when it fades to a peach color. RHS 36B and 36C FIG. 3. Close up of the flower when it fades to a pink. RHS 48C FIG. 4. A group picture showing all three colors.

DETAILED BOTANICAL DESCRIPTION

In the following description, color references are made to The Royal Horticultural Society Colour Chart (2001). Plants used for the description were grown in a field for two years at a nursery in Hebron, Ill. Measurements and numerical values represent averages of typical plants.

Botanical classification: *Geum* hybrid cultivar Mai Tai

Parentage: Female or seed *Geum* 'Flames of Passion' U.S. Pat. No. 13,730 and male or pollen *Geum* 'Mango Lassi'.

Propagation: Vegetative division.

Plant description: Overall habit of the new *Geum* is basal clumps, upright flower stems topped by single and semi double flowers that open vermilion RHS 53B then fade to peach RHS 36B and 36C and then finally fade to pink RHS 48C.

*Plant height.*—35 cm.

*Plant width.*—30-35 cm.

*Stem.*—Diameter: 3-4 mm.

*Stem or basal branches.*—Length up to 42 cm, with the internode between basal foliage and first leaflet length being 9-11 cm and the second internode between the first leaflet and the second leaflet length being 6-10 cm and the third internode between the second and third leaflet length being 7-8 cm.

*Stem coloration.*—Of the base of the stem is close to 145A and 145B, coloration of the top of the stem is N77A.

Foliage description:

*Type.*—Deciduous.

*Arrangement.*—Basal alternate with typically two or three lateral leaflets per stem.

*Petiole.*—Up to 7-9 cm long, with a diameter of 5 mm, color close to N144.

*Terminal compound leaf length.*—Up to 20 cm.

*Terminal compound leaf width.*—8 cm.

*Terminal leaflet length.*—Typically 4-5 cm.

*Terminal leaflet width.*—Typically 3-4 cm.

*Terminal Leaflet shape.*—Obovate with incised margins.

*Terminal and lateral leaf apex.*—Acute.

*Terminal and lateral leaf base.*—Cuneate.

*Terminal and lateral leaf margin.*—Incised.

*Texture.*—Terminal and lateral leaf, upper and lower surfaces: pubescent.

*Venation pattern.*—Terminal and lateral leaf, upper and lower surfaces: pinnate.

*Venation color.*—Terminal and lateral leaf, upper surface is color 137 B and lower surface color is 137 C.

*Lateral leaflet number.*—2 or 3 per stem.

*Lateral leaflet length.*—1-2 cm.

*Lateral leaflet width.*—Up to 1 cm.

*Lateral leaflet shape.*—Obovate.

*Adaxial leaf description.*—Color is 146 A.

*Abaxial leaf description.*—Color 138 B.

Flower description:

*Flower type.*—Solitary.

*Flower color.*—53 B then fade to 36B and 36C and finally into 48 C.

*Flower size.*—Diameter: 25-30 mm across, depth 10-15 mm.

*Flower number.*—4-5 per stem, 90-135 per plant.

*Number flowering stems.*—20-30.

*Bloom period and duration.*—Beginning May into June in Hebron, Ill.

*Flower longevity and duration on the plant.*—Approximately 3 weeks.

*Flower longevity and duration cut.*—Not measured.

*Scent.*—None.

*Petal count.*—10-20.

*Petal shape.*—Spatulate.

*Petal arrangement.*—Rotate, overlapping.

*Petal diameter or width.*—12 mm across and petal length — 10 mm long.

*Petal apex.*—Retuse, base: attenuate, margin: entire.

*Petal texture.*—Upper and lower surfaces: smooth, glabrous.

*Petal color.*—Upper surface is color 53B fade into 36B and 36C and then 48C.

*Petal color.*—Lower surface color was 27B to 27D.

*Inflorescence diameter and height.*—8-12 cm across, 10 cm long.

*Flower buds.*—Diameter: 10-12 mm across, depth: 10 mm, shape: ovoid, surface: slightly pubescent and color between 59A and 59B.

*Sepal size.*—Length: up to 14 mm, diameter: 6 mm at base coming to a point.

*Sepal quantity.*—6.

*Sepal shape.*—Lanceolate, apex: acute, base: cuneate, margin: entire.

*Sepal texture.*—Upper and lower surfaces: Pubescent.

*Sepal color.*—Adaxial color was not found using the RHS color chart, Abaxial color 59 A.

*Peduncle color.*—Purple N 77 A.

*Peduncle size.*—Length: 20-25 mm, diameter: 3 mm.

*Pedicel size.*—Length: 4-8 cm, diameter: 1-2 mm and color N77 A.

*Reproductive organs.*—Stamen — quantity over 100, length 1 cm.

*Anther.*—Quantity: over 100, length: 1 mm, diameter: close to 0.5 mm.

*Pollen.*—Typically present, color: 12A.

*Stigma.*—None observed.

*Style.*—Number: over 50 length: 6 mm.

*Pistil.*—Number: over 50, length: 6+ mm.

*Ovaries.*—None observed.

*Fruit.*—None observed.

Disease resistance: Resistance to diseases common to *Geum* has not been observed on plants grown under nursery conditions.

I claim:

1. A new, distinct *Geum* plant as shown and described, characterized by single and semi double flowers that open vermilion then fade to peach and then finally fade to pink.

* * * * *